United States Patent

Butwell et al.

[11] Patent Number: 5,928,268
[45] Date of Patent: Jul. 27, 1999

[54] CURVED SURGICAL NEEDLES AND METHOD OF MAKING THE SAME

[75] Inventors: Richard A. Butwell; Robert A. Hlavacek, both of Naugatuck; Carl Monti, Brookfield, all of Conn.

[73] Assignee: Tyco Group S.a.r.l., Luxembourg

[21] Appl. No.: 08/993,759

[22] Filed: Dec. 18, 1997

[51] Int. Cl.[6] .................................................. A61B 17/04
[52] U.S. Cl. ............................................. 606/222; 163/5
[58] Field of Search ....................... 606/222, 223; 163/5; 29/402.19; 72/379.2, 379.6

[56] References Cited

U.S. PATENT DOCUMENTS

| 3,038,475 | 6/1962 | Orcutt | 606/223 |
|---|---|---|---|
| 4,534,771 | 8/1985 | Dilling | 8/524 |
| 5,178,628 | 1/1993 | Otsuka et al. | 606/223 |
| 5,330,441 | 7/1994 | Prasad et al. | 606/222 |
| 5,342,397 | 8/1994 | Guido | 606/222 |
| 5,749,897 | 5/1998 | Matsutani et al. | 606/222 |

*Primary Examiner*—Gary Jackson
*Attorney, Agent, or Firm*—Montgomery W. Smith

[57] ABSTRACT

A curved surgical needle and a method for producing the same from a solid sheet of material rather than from coiled wire including the steps of drilling a bore in one edge of the material, grinding an edge opposite the drilled edge to form a sharpened point, curving the material and cutting the material at a point of equal distance between each drilled bored to provide a surgical needle. A suture is then attached to the surgical needle, optionally lubricated, sterilized, and packaged by suitable means known in the art.

5 Claims, 5 Drawing Sheets

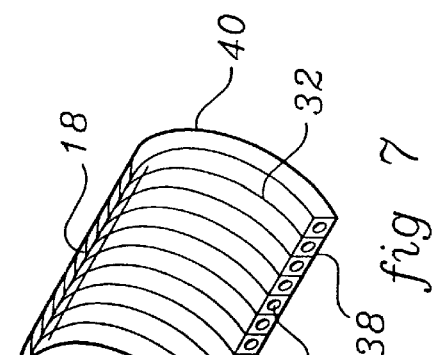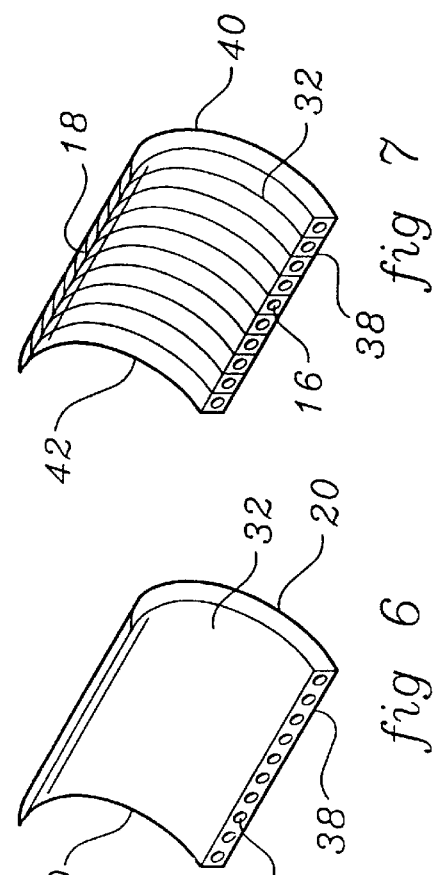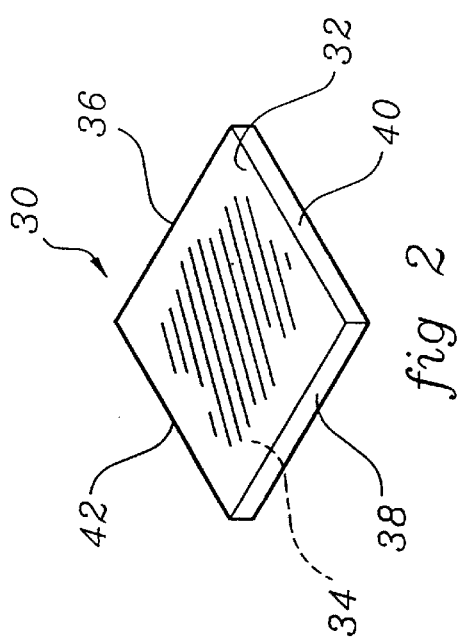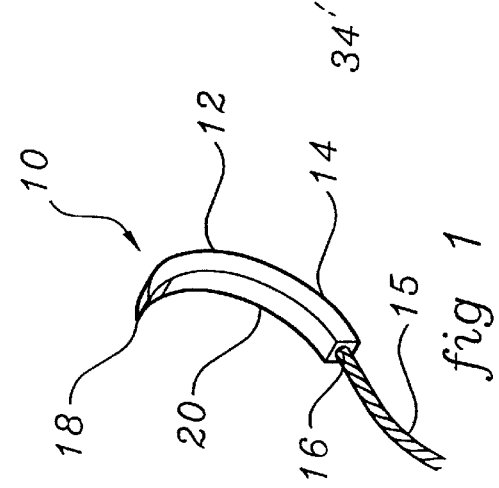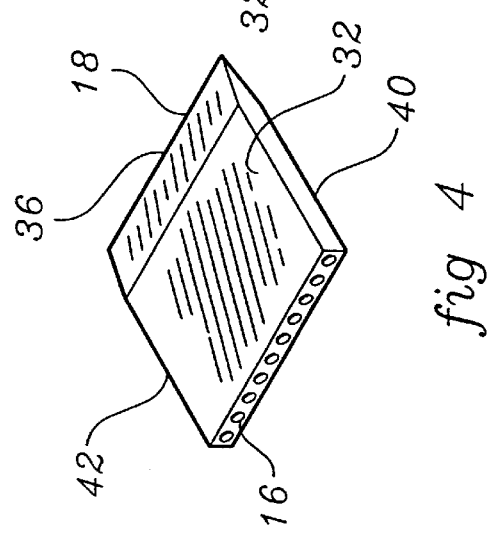

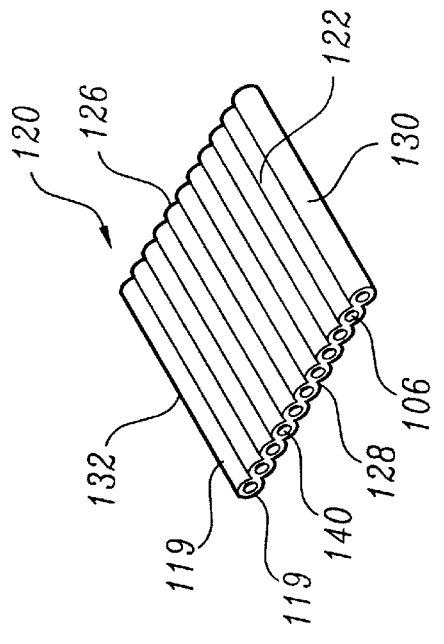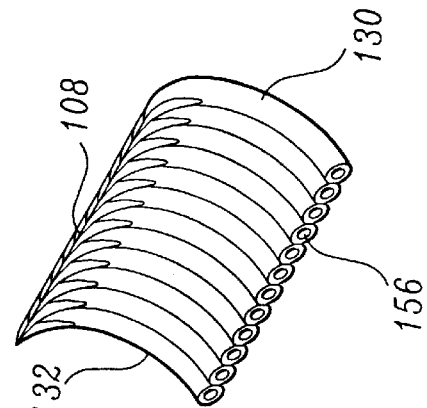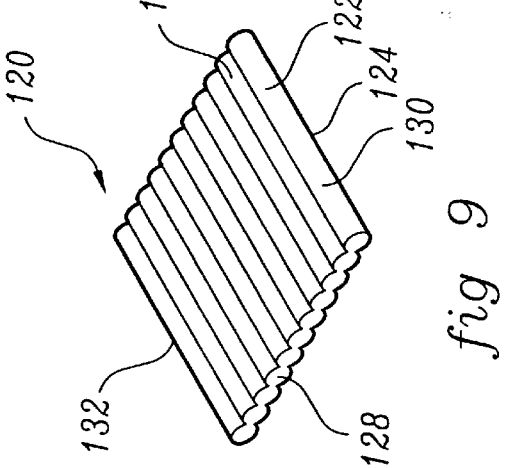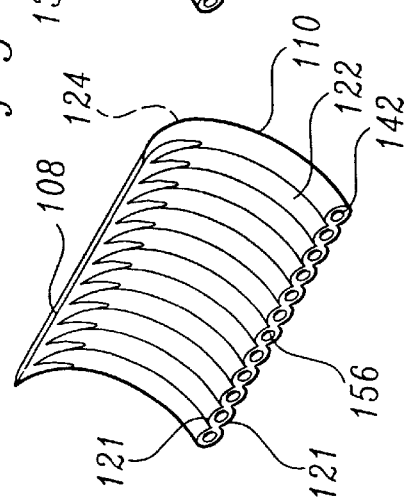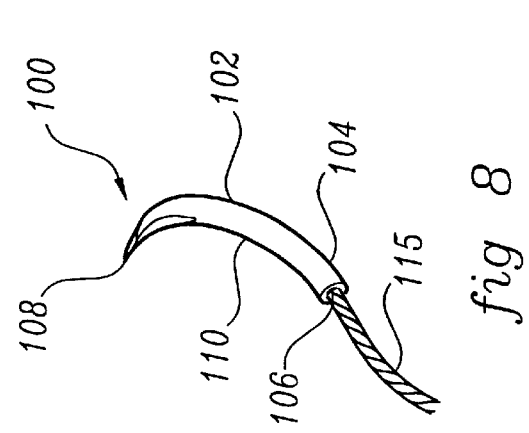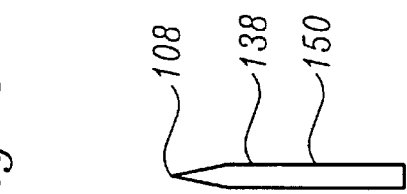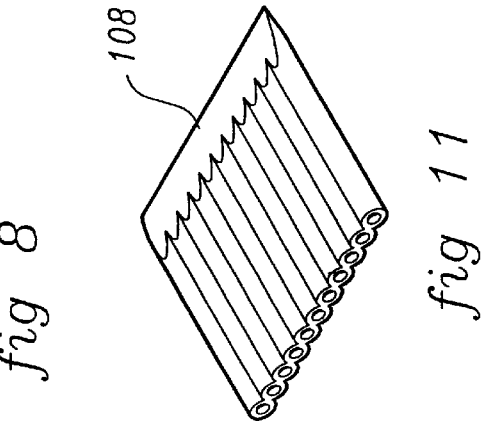

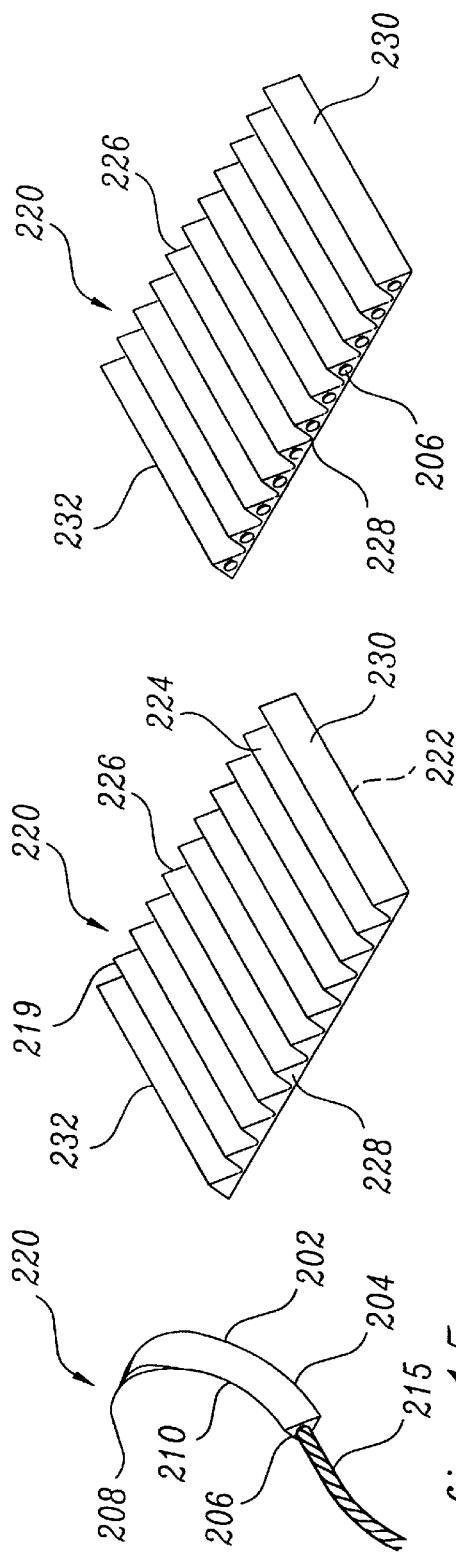

CURVED SURGICAL NEEDLES AND METHOD OF MAKING THE SAME

FIELD OF THE INVENTION

The present invention relates to a curved bodied surgical needle and a method of manufacturing the same and more particularly to curved rectangular, round, oval or triangular bodied surgical needles produced from a planar, corrugated or planar and corrugated sheet material.

BACKGROUND OF THE INVENTION

The production of needles from wire stock involves many processes and different types of machinery in order to prepare quality needles. These varying processes and machinery become more critical in the preparation of surgical needles where the environment of intended use is in humans or animals. Some of the processes involved in the production of surgical grade needles include, straightening spooled wire stock, cutting needle blanks from raw wire stock, tapering or grinding points on one end of the blank stock, providing a bore for receiving suture thread at the other end of the blank stock, imparting flat pressed surfaces on opposite sides of the blank by flat pressing a portion of the needle blank to facilitate grasping by surgical instrumentation and the curving of the needle where curved needles are desired. Additional processing may be done to impart flat surfaces substantially perpendicular to the flat pressed portions of the needle blank by side pressing a portion of the needle blank to further facilitate grasping by surgical instrumentation and insertion into humans or animals. Conventional needle processing is, in large part, a labor intensive operation requiring highly skilled labor. Generally, extreme care must be taken to insure that only the intended working of the needle is performed and the other parts of the needle remain undisturbed. Curved rectangular bodied needles have advantages over other needle configurations in many surgical procedures for a variety of reasons including, uniformity of entry depth for multiple sutures and proper "bite" of tissue surrounding the incision or wound. When providing curved bodied needles for surgical procedures, it is desirable for the needles to have a specified cross section and a specified curvature, i.e., a predetermined radius of curvature. The desired cross section and radius of curvature for the finished needle varies with specific applications as is known in the art.

Known methods of forming curved rectangular bodied needles require several separate and distinct operations to be performed on various machinery. The needle blank after having been cut from straightened wire stock must be flat pressed to impart opposed flat surfaces along body portions located between a tapered point end and a drilled end of the needle blanks. After flat pressing to form opposed flat surfaces on the needle blank, the needle can then be taken from the flat press dies to a curving machine to impart the proper curvature to the needle blank. Optionally, the flat pressing and curving of the needle blank may be accomplished in one step with some available curving die equipment. Care must be taken when removing the blanks from the flat press dies and the curving machinery to avoid disturbing the flat surfaces imparted to the needle blank. After the curving and flat pressing the needle blanks, the needle can then be taken from the curving anvil or die to a side press station to impart flat surfaces substantially perpendicular to the opposed flat surfaces previously formed to give the final rectangular cross sectional profile to the needle body. Again, care must be taken during removal of the needle blanks from the curving anvil and during side flat pressing so as to avoid disturbing the previously imparted opposed flat surface and curved portions of the needle blank.

When needles are made of steel or similar resilient materials, the anvil, die or mandrel used to impart curvature to the needle should have a smaller radius than the radius desired in the final needle product. This configuration allows for some springback after the bending operation and insures that the desired radius of curvature is obtained. Disclosure of such features may be found in U.S. Pat. No. 4,534,771. Previously flattened surgical needles improperly positioned on the anvil for curving may result in a deformation of the previously imparted opposed flat surfaces and may have to be reprocessed or discarded.

One disadvantage to the conventional needle forming techniques noted above is that typically only one needle processing operation at a time, such as, for example, wire straightening, blank cutting, sharpening, boring, flat pressing, curving, can be performed on a single piece of machinery. A further disadvantage is the long processing time required to produce such a needle and the high cost associated with forming and transporting the needles between the various machinery. Lastly, a still further disadvantage is the need to readjust numerous pieces of machinery to process needles of varying length and diameters which further increases production tooling down time and production costs. Therefore, a need exists for a surgical needle forming process that is capable of eliminating one or more processing operations such as flat wire straightening, blank cutting, flat pressing, curving, or side pressing needle blanks. It is also desirable to provide a method of forming curved bodied needles which reduces the time required to produce such needles and the associated costs. It is also desirable to provide a process for producing curved bodied needles which decreases material handling demands.

SUMMARY OF THE INVENTION

The present invention provides a curved rectangular, round, oval or triangular bodied surgical needle and a method for producing curved rectangular, round, oval, or triangular bodied surgical needles for use in human or animal surgical procedures. The preferred method of producing a curved rectangular bodied surgical needle according to the present invention includes obtaining a flat or planar rectangular or square material sheet of predetermined composition and dimensions, drilling at least two holes into one edge of the material sheet, grinding one edge opposed to the drilled edge of the material sheet, curving the material sheet, and cutting the material sheet at a point of equal distance between each drilled hole to produce a curved rectangular bodied surgical needle.

The preferred method of producing a curved round bodied surgical needle according to the present invention includes obtaining a rectangular or square material sheet of predetermined composition and dimensions, having opposed corrugated surfaces, drilling at least two holes into one edge of the material sheet, grinding one edge opposed to the drilled edge of the material sheet, curving the material sheet, and cutting the material sheet at a point of equal distance between each drilled hole corresponding to the grooves of the corrugated surface of the material to produce curved round bodied surgical needles.

The preferred method of producing a curved oval bodied surgical needle according to the present invention includes obtaining a rectangular or square material sheet of predetermined composition and dimensions, having opposed corrugated surfaces, drilling at least two holes into one edge of the material sheet, grinding one edge opposed to the drilled edge of the material sheet, curving the material sheet, and cutting the material sheet at a point of equal distance between each drilled hole corresponding to the grooves of the corrugated surface of the material to produce curved oval bodied surgical needles.

The preferred method of producing a curved triangular bodied surgical needle according to the present invention, includes obtaining a rectangular or square material sheet of predetermined composition and dimensions, having one smooth planar surface and one corrugated surface, drilling at least two holes into one edge of the material sheet, grinding one edge opposed to the drilled edge of the material sheet, curving the material sheet, and cutting the material sheet at a point of equal distance between each drilled hole corresponding to the grooves of the corrugated surface of the material to produce curved triangular bodied surgical needles.

Accordingly, it is a primary objective of the present invention to provide a method for producing surgical needles which decreases production time. It is a further object of the present invention to provide a more economical method for producing curved rectangular, round, oval or triangular bodied surgical needles. It is a further object of the present invention to provide a method for producing surgical needles which minimizes potential damage thereto. It is a further object of the present invention to provide a method of producing surgical needles which is compatible with existing surgical suture attachment methods and equipment.

Other objects, features, and advantages of the present invention shall become apparent in view of the following description when considered in connection with the accompanying illustrative drawings.

DESCRIPTION OF THE DRAWINGS

In the drawings which illustrate the best mode presently contemplated for carrying out the present invention:

FIG. 1 is a perspective view of a curved rectangular bodied surgical needle;

FIG. 2 is a perspective view of a sheet of stainless steel material of predetermined dimensions;

FIG. 3 is a perspective view of the material sheet of FIG. 2 having apertures drilled in an edge thereof;

FIG. 4 is a perspective view of the material sheet of FIG. 3 having an edge thereof ground to a surgical point;

FIG. 5 is a side edge view of the material sheet of FIG. 4;

FIG. 6 is a perspective view of the material sheet of FIG. 4 after curvature thereof;

FIG. 7 is a perspective view of the material sheet of FIG. 6 after having been cut into a plurality of surgical needles;

FIG. 8 is a perspective view of a curved round bodied surgical needle;

FIG. 9 is a perspective view of a sheet of corrugated stainless steel material of predetermined dimensions;

FIG. 10 is a perspective view of the corrugated material sheet of FIG. 9 having apertures drilled in an edge thereof between grooves;

FIG. 11 is a perspective view of the corrugated material sheet of FIG. 10 having an edge thereof ground to a surgical point;

FIG. 12 is a side edge view of the corrugated material sheet of FIG. 11;

FIG. 13 is a perspective view of the corrugated material sheet of FIG. 11 after curvature thereof;

FIG. 14 is a perspective view of the corrugated material sheet of FIG. 13 after having been cut into a plurality of surgical needles;

FIG. 15 is a perspective view of a curved triangular bodied surgical needle;

FIG. 16 is a perspective view of a sheet of corrugated and planar stainless steel material of predetermined dimensions;

FIG. 17 is a perspective view of the corrugated and planar material sheet of FIG. 16 having apertures drilled in an edge thereof between grooves;

FIG. 18 is a perspective view of the corrugated and planar material sheet of FIG. 17 having an edge thereof ground to a surgical point;

FIG. 19 is a side edge view of the corrugated and planar material sheet of FIG. 18;

FIG. 20 is a perspective view of the corrugated and planar material sheet of FIG. 18 after curvature thereof;

FIG. 21 is a perspective view of the corrugated and planar material sheet of FIG. 20 after having been cut into a plurality of surgical needles;

DESCRIPTION OF THE INVENTION

Figure 23:
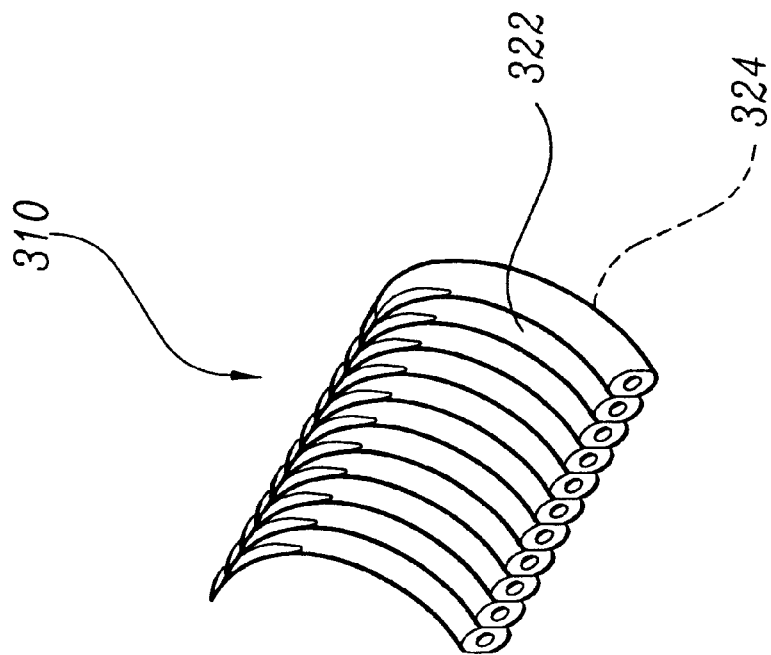
FIG. 23 is a perspective view of a sheet of stainless steel material of predetermined dimensions.

Referring to the drawings, the preferred embodiment of the curved rectangular bodied surgical needle of the present invention is illustrated and generally indicated as 10 in FIG. 1. The curved rectangular bodied surgical needle of the present invention 10 comprises a body portion 12 which is curved to fall within a range of curvature between 90 and 180 degrees. The needle has a blunt end 14 having an aperture 16 therein suitable for accepting a suture 15 by means of a suitable adhesive, polymeric attachment means, friction fit, or like methods known in the art. Preferably, a suture is attached to the needle 10 by means of a drilled aperture 16 in blunt end 14 which may be crimped to hold the suture 15 but is not intended to be limited thereto. Opposed to blunt end 14 of body portion 12 is a sharpened point 18 suitable for the penetration of human or animal tissue. The curved portion 20 of body portion 12 preferably has a rectangular cross section of predetermined dimensions. The overall size or length of the surgical needle can cover the full range of sizes known to those skilled in the art such as from approximately 5 to 50 millimeters in length but preferably approximately 10 to 47 millimeters in length for greater manageability.

Surgical needle 10 of the present invention may be made from any of the various steels known in the art to be suitable for surgical needles, such as, but not limited to, stainless steels containing chromium. The preferred material for the needles of the present invention are 300 or 400 series stainless steels due to superior strength and durability.

The surgical needles 10 of the present invention are produced using an unique method illustrated in FIGS. 2 through 7.

Figure 24:
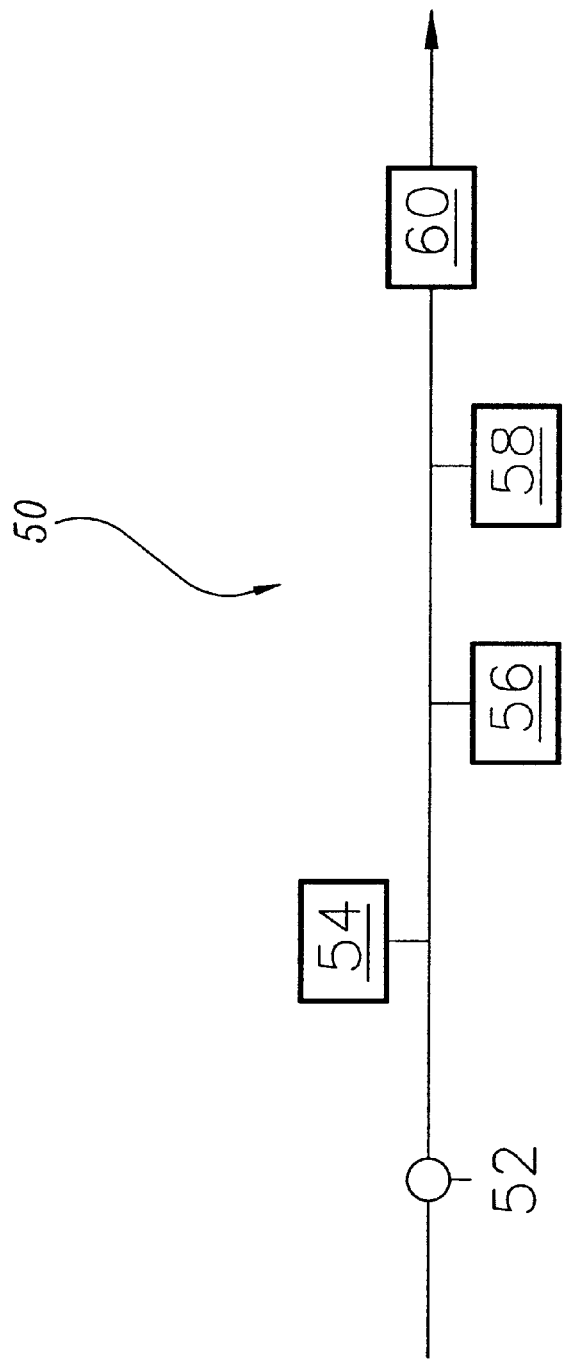
FIG. 24 is a schematic diagram of a process for producing curved surgical needles of the present invention.

A material sheet generally indicated as 30 in FIGS. 2 through 7 used in producing curved rectangular bodied surgical needles 10 comprises upper and lower smooth planner surfaces 32 and 34 respectively, point edge 36, blunt edge 38, and side edges 40 and 42. Material sheet 30 is preferably dimensioned between approximately one half and one and one half but preferably approximately 1 1/16th of an inch in length measuring between point and blunt edges 36 and 38 respectively, between approximately 40 and 60 inches but preferably approximately 48 inches in width measuring between side edges 40 and 42 and between approximately 0.01 and 0.1 of an inch but preferably approximately 0.02 of an inch in thickness measuring between planar surfaces 32 and 34. The dimensions of the material sheet, however, are variable depending on the number of needles to be made per sheet and the desired final dimensions of the surgical needle product. Once the material sheet is obtained in the desired dimensions or cut, honed and/or machined to the desired dimensions, the material sheet is then clamped by a gripping means portion 52, schematically illustrated in FIG. 24, of a machining apparatus, illustrated generally as 50 in FIG. 24. The gripping means portion 52 is designed to move towards a drilling device portion 54 of the machining apparatus 50 for the drilling of an aperture 16 in blunt edge 38 of sheet material 30, and then retract. The gripping means portion 52 then progresses a predetermined distance before again approaching the drilling device portion 54 to drill the next aperture 16 in the blunt edge 38 of sheet material 30. The resulting sheet has apertures or bores 16 drilled in blunt edge 38 at predetermined distances as best illustrated in FIG. 3. The sheet material 30 still clamped by the gripping means portion 52 progresses to a grinding position 56 whereby point edge 36 is ground by preferably a rotating abrasive means so as to form sharpened point 18 as illustrated in FIGS. 4 and 5. The material sheet 30 then progresses to a die stamp or mandrel belt apparatus and sheet material 30 is bent to form a curved portion 20 of the appropriate curvature as illustrated in FIG. 6. At this point, material sheet 30 passes to a cutting apparatus 60 whereby sheet material 30 is cut at a point of equal distance between each drilled aperture as illustrated in FIG. 7. The resultant surgical needle 10 may then be polished and/or electrohoned in order to deburr, soften edges and/or polish the needle which is then ready for any optional point modification, suture attachment, optional lubrication, sterilization and packaging as discussed in greater detail below.

After the curved rectangular bodied surgical needle 10 has been so produced in accordance with the present invention, a suture 15 may be attached by any suitable method currently known to those skilled in the art. Optionally, the curved rectangular bodied surgical needle 10 is lubricated before being sterilized and packaged. It is important to note that any suitable optional point modification, suture attachment means, optional lubrication process, sterilization process, and packaging currently known in the art may be used in accordance with the curved rectangular bodied surgical needle of the present invention.

Referring to the drawings, the preferred embodiment of the curved round bodied surgical needle of the present invention is illustrated and generally indicated as 100 in FIG. 8. The curved round bodied surgical needle 100 of the present invention comprises a body portion 102 which is curved to fall within a range of curvature between 90 and 180 degrees. The needle has a blunt end 104 having an aperture 106 therein suitable for accepting a suture 115 by means of a suitable adhesive, polymeric attachment means, friction fit, or like methods known in the art. Preferably, a suture 115 is attached to the needle 100 by means of a drilled aperture 106 in blunt end 104 which may be crimped to hold the suture but is not intended to be limited thereto. Opposed to blunt end 104 of body portion 102 is a sharpened point 108 suitable for the penetration of human or animal tissue. The curved portion 110 of body portion 102 preferably has a round cross section of predetermined diameter. The overall size or length of the surgical needle can cover the full range of sizes known to those skilled in the art such as from approximately 5 to 50 millimeters in length but preferably approximately 10 to 47 millimeters in length for greater manageability.

Surgical needle 100 of the present invention may be made from any of the various steels known in the art to be suitable for surgical needles, such as, but not limited to, stainless steels containing chromium. The preferred material for the needles of the present invention are 300 or 400 series stainless steels due to superior strength and durability.

The surgical needles 100 of the present invention are produced using an unique method illustrated in FIGS. 9 through 14.

A material sheet generally indicated as 120 in FIGS. 9 through 14 used in producing curved round bodied surgical needles 100 comprises upper and lower corrugated surfaces 122 and 124 respectively, point edge 126, blunt edge 128, and side edges 130 and 132. Material sheet 120 is preferably dimensioned between approximately one half and one and one half inch but preferably approximately 1 1/16th of an inch in length measuring between point and blunt edges 126 and 128 respectively, between approximately 40 and 60 inches but preferably approximately 48 inches in width measuring between side edges 130 and 132 and between approximately 0.01 and 0.1 of an inch but preferably approximately 0.02 of an inch in thickness measuring between the peaks 119 of upper and lower corrugated surfaces 122 and 124, respectively. The dimensions of the material sheet, however, are variable depending on the number of the needles to be made per sheet and the desired final dimensions of the surgical needle product. Once the material sheet is obtained in the desired dimensions or cut, honed and/or machined to the desired dimensions, the material sheet is then clamped by a gripping means portion 52, schematically illustrated in FIG. 24, of a machining apparatus illustrated generally as 50 in FIG. 24. The gripping means portion 52 is designed to move towards a drilling device portion 54 of the machining apparatus 50 for the drilling of an aperture 106 in blunt edge 128 of sheet material 120, and then retract. The gripping means portion 52 then progresses a predetermined distance before again approaching the drilling device portion 54 to drill the next aperture 106 into blunt edge 128 of sheet material 120. The resulting sheet has apertures or bores 106 drilled in blunt edge 128 at predetermined distances as best illustrated in FIG. 10. The sheet material 120 still clamped by the gripping means portion 52 progresses to a grinding position 56 whereby point edge 126 is preferably ground by a rotating abrasive means so as to form sharpened point 108 as illustrated in FIGS. 11 and 12. The material sheet 120 then progresses to a die stamp or mandrel belt apparatus 58 and sheet material 120 is bent to form a curved portion 110 of the appropriate curvature as illustrated in FIG. 13. At this point, material sheet 120 passes to a cutting apparatus 60 whereby sheet material 120 is cut at a point of equal distance between each drilled aperture corresponding with the grooves 121 of upper and lower corrugated surfaces 122 and 124 respectively, as illustrated in FIG. 14. The resultant surgical needle 100 may then be polished and/or electrohoned in order to deburr, soften edges and/or polish the needle which is then ready for any optional point modification, suture attachment, optional lubrication, sterilization and packaging as discussed in greater detail below.

After the curved round bodied surgical needle 100 has been so produced in accordance with the present invention, a suture 115 may be attached by any suitable method currently known to those skilled in the art. Optionally, the curved round bodied surgical needle 100 is lubricated before being sterilized and packaged. It is important to note that any suitable optional point modification, suture attachment means, optional lubrication process, sterilization process, and packaging currently known in the art may be used in accordance with the curved round bodied surgical needle of the present invention.

Figure 22:
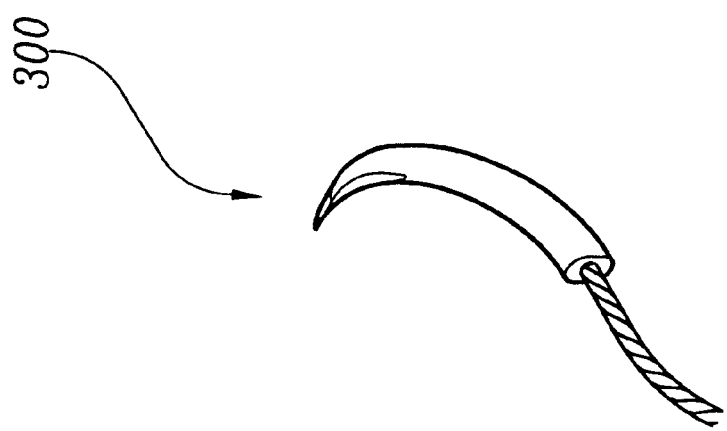
FIG. 22 is a perspective view of a curved oval bodied surgical needle.

It should be noted that curved oval bodied surgical needles 300 illustrated best in FIG. 22 can be produced using the above-described process for producing round bodied needles by varying the corrugation of upper and lower corrugated surfaces 322 and 324 respectively, of sheet material 320 as illustrated in FIG. 23.

Referring to the drawings, the preferred embodiment of the curved triangular bodied surgical needle of the present invention is illustrated and generally indicated as 200 in FIG. 15. The curved triangular bodied surgical needle of the present invention 200 comprises a body portion 202 which is curved to fall within a range of curvature between 90 and 180 degrees. The needle has a blunt end 204 having an aperture 206 therein suitable for accepting a suture 215 by means of a suitable adhesive, polymeric attachment means, friction fit, or like methods known in the art. Preferably, a suture 215 is attached to the needle by means of a drilled aperture 206 in blunt end 204 which may be crimped to hold the suture 215 but is not intended to be limited thereto. Opposed to blunt end 204 of body portion 202 is a sharpened point 208 suitable for the penetration of human or animal tissue. The curved portion 210 of body portion 202 preferably has a triangular cross section of predetermined dimensions. The overall size or length of the surgical needle can cover the full range of sizes known to those skilled in the art such as from approximately 5 to 50 millimeters in length but preferably approximately 10 to 47 millimeters in length for greater manageability.

Surgical needle 200 of the present invention may be made from any of the various steels known in the art to be suitable for surgical needles, such as, but not limited to, stainless steels containing chromium. The preferred material for the needles of the present invention are 300 or 400 series stainless steels due to superior strength and durability.

The surgical needles 200 of the present invention are produced using an unique method illustrated in FIGS. 16 through 21.

A material sheet generally indicated as 220 in FIGS. 16 through 21 used in producing curved triangular bodied surgical needles 200 comprises a lower planner surface 222 an upper corrugated surface 224, point edge 226, blunt edge 228, and side edges 230 and 232. Material sheet 220 is preferably dimensioned between approximately one half and one and one half inches but preferably approximately 1 1/16th inches in length measuring between point and blunt edges 226 and 228, respectively, between approximately 40 and 60 inches but preferably approximately 48 inches in width measuring between side edges 230 and 232 and approximately 0.01 and 0.1 of an inch, but preferably approximately 0.02 of an inch in thickness measuring between lower planar surface 222 and the peak 219 of corrugated upper surface 224. The dimensions of the material sheet, however, are variable depending on the number of the needles to be made per sheet and the desired final dimensions of the surgical needle product. Once the material sheet is obtained in the desired dimensions or cut, honed and/or machined to the desired dimensions, the material sheet is then clamped by a gripping means portion 52, schematically illustrated in FIG. 24, of a machining apparatus illustrated generally as 50 in FIG. 24. The gripping means portion 52 is designed to move towards a drilling device portion of the machining apparatus 50 for the drilling of an aperture 206 in blunt edge 228 of sheet material 220, and then retract. The gripping means portion 52 then progresses a predetermined distance before again approaching the drilling device portion 54 to drill the next aperture 206 into blunt edge 228 of the sheet material 220. The resulting sheet has apertures or bores 206 drilled in blunt edge 228 at predetermined distances as best illustrated in FIG. 17. The sheet material 220 still clamped by the gripping means portion 52 progresses to a grinding position 56 whereby point edge 226 is ground preferably by a rotating abrasive means so as to form sharpened point 208 as illustrated in FIGS. 18 and 19. The material sheet 220 then progresses to a die stamp or mandrel belt apparatus 58 and sheet material 220 is bent to form a curved portion 210 of the appropriate curvature as illustrated in FIG. 20. At this point, material sheet 220 passes to a cutting apparatus 60 whereby sheet material 220 is cut at equal distances between each drilled aperture corresponding with the grooves 219 of upper corrugated surface 224 as illustrated in FIG. 21. The resultant surgical needle 200 may then be polished and/or electrohoned in order to deburr, soften edges and/or polish the needle which is then ready for any optional point modification, suture 215 attachment, optional lubrication, sterilization and packaging as discussed in greater detail below.

After the curved triangular bodied surgical needle 200 has been so produced in accordance with the present invention, a suture 15 may be attached by any suitable method currently known to those skilled in the art. Optionally, the curved rectangular bodied surgical needle 200 is lubricated before being sterilized and packaged. It is important to note that any suitable optional point modification, suture attachment means, optional lubrication process, sterilization process, and packaging currently known in the art may be used in accordance with the curved triangular bodied surgical needle of the present invention.

It is unexpected that it would be possible to produce the present curved bodied surgical needles in accordance with the method disclosed herein for use in humans and animals due to the small size of the needles required for human and animal surgical use. The cutting of surgical needles from a planar, corrugated and/or planar and corrugated material sheet has been found to be achievable as disclosed herein. The curved bodied surgical needles produced according to the teachings of the present invention are an advantage over needles produced from processes currently known in the art since numerous production steps have been eliminated to decrease the costs of production and lessen the potential for damaging the needle.

Having now described the invention, it should be readily apparent that many variations and modifications may be made without departing from the spirit and scope of the present invention.

What is claimed is:

1. A method of producing a stainless steel surgical needle comprising drilling at least two bores within an edge of a solid material sheet, grinding an edge opposite said drilled edge to form a sharpened point, curving the material sheet and cutting the material sheet at a point of equal distance between each drilled bore to form a surgical needle.

2. The method of claim 1 where in said needle has a rectangular cross-section.

3. The method of claim 1 where in said needle has a round cross-section.

4. The method of claim 1 where in said needle has an oval cross-section.

5. The method of claim 1 where in said needle has a triangular cross-section.

* * * * *